(12) United States Patent
Oh et al.

(10) Patent No.: US 10,724,015 B2
(45) Date of Patent: Jul. 28, 2020

(54) MICROORGANISM HAVING IMPROVED ABILITY TO PRODUCE N-ACETYLGLUCOSAMINE AS A RESULT OF MODULATING GLYCOLYTIC FLUX

(71) Applicant: Korea University Research and Business Foundation, Seoul (KR)

(72) Inventors: Min-Kyu Oh, Gyeonggi-do (KR); Sang-Woo Lee, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 7 days.

(21) Appl. No.: 15/598,045

(22) Filed: May 17, 2017

(65) Prior Publication Data
US 2017/0335358 A1    Nov. 23, 2017

(30) Foreign Application Priority Data

May 18, 2016  (KR) .................... 10-2016-0060920
May 15, 2017  (KR) .................... 10-2017-0059916

(51) Int. Cl.
| | |
|---|---|
| *C12P 13/00* | (2006.01) |
| *C12N 9/12* | (2006.01) |
| *C12N 9/10* | (2006.01) |
| *C12P 19/26* | (2006.01) |

(52) U.S. Cl.
CPC ......... *C12N 9/1205* (2013.01); *C12N 9/1096* (2013.01); *C12P 19/26* (2013.01); *C12Y 206/01016* (2013.01); *C12Y 207/0104* (2013.01); *C12Y 207/01011* (2013.01); *C12Y 207/01105* (2013.01)

(58) Field of Classification Search
None
See application file for complete search history.

(56) References Cited

U.S. PATENT DOCUMENTS 7,332,304 B2 *  2/2008  Deng .................... C12N 15/52
                                                        435/15

FOREIGN PATENT DOCUMENTS

| KR | 1020050053534 A | 6/2005 |
|---|---|---|
| KR | 1020100044129 A | 4/2010 |

(Continued)

OTHER PUBLICATIONS

Boles et al. Yeast vol. 9, pp. 761-770, 1993.*

(Continued)

*Primary Examiner* — Richard G Hutson
(74) *Attorney, Agent, or Firm* — Hultquist, PLLC; Steven J. Hultquist

(57) ABSTRACT

The present invention relates to a mutant microorganism in which a gene that encodes phosphofructokinase-2 is disrupted or deleted to reduce glycolytic flux to thereby improve the ability of the microorganism to produce N-acetylglucosamine, and to a method of producing N-acetylglucosamine using the mutant microorganism. The mutant microorganism according to the present invention has advantages in that it has high resistance to various chemical substances, grows rapidly, is easily cultured, and produces N-acetylglucosamine with high efficiency, indicating that it is useful for production of a large amount of N-acetylglucosamine.

9 Claims, 5 Drawing Sheets
(5 of 5 Drawing Sheet(s) Filed in Color)
Specification includes a Sequence Listing.

(56) References Cited

FOREIGN PATENT DOCUMENTS

| KR | 10-2016-0002509 A | 1/2016 | |
|---|---|---|---|
| WO | WO-2012097091 A2 * | 7/2012 | ............... C12N 9/92 |

OTHER PUBLICATIONS

Ngo et al. in The Protein Folding Problem and Tertiary Structure Prediction, 1994, Merz et al. (ed.), Birkhauser, Boston, MA, pp. 433 and 492-495/.*

Lee et al., ("2013 KSBB Fall Meeting and International Symposium Presentation and Poster", Oct. 16-18, pp. 1-46, Published in Busan, Republic of Korea) (Year: 2013).*

Bloes, E., et al., "Cloning of a Second Gene Encoding 6-phosphofructo-2-kinase in Yeast, and Characterization of Mutant Strains Without Fructose-2,6-bisphosphate", "Molecular Microbiology", 1996, pp. 65-76, vol. 20, No. 1.

Daldal, F., et al., "An Alteration in Phosphofructokinase 2 of *Escherichia coli* Which Impairs Gluconeogenic Growth and Improves Growth in Sugars", "European J. Biochem.", 1982, pp. 373-379, vol. 126.

Lee, S., et al., "A Synthetic Suicide Riboswitch for the High-Throughput Screening of Metabolite Production in *Saccharomyces cerevisiae*", "Metabolic Engineering", 2015, pp. 143-150, vol. 28.

Liu, Y., et al., "Pathway Engineering of Bacillus Subtilis for Microbioal Production of N-Acetylglucosamine", "Metabolic Engineering", 2013, pp. 107-115, vol. 19.

Payne, V., et al., "Dual Role of Phosphofructokinase-2/Fructose Bisphosphatase-2 in Regulating the Compartmentation and Expression of Glucokinase in Hepatocytes", "Diabetes", 2005, pp. 1949-1957, vol. 54.

Ros, S., et al., "Balancing Glycolytic Flux: the Role of 6-phosphofructo-2-kinase/fructose 2,6-bisphosphatases in Cancer Metabolism", "Cancer and Metabolism", 2013, pp. 1-10, vol. 1, No. 8.

Brachmann, C.B., et al., "Designer Deletion Strains derived from *Saccharomyces cerevisiae* S288C: a Useful set of Strains and Plasmids for PCR-mediated Gene Disruption and Other Applications", "Yeast", 1998, pp. 115-132, vol. 14, No. 2.

Farzadfard, F., et al., "Tunable and Multifunctional Eukaryotic Transcription Factors Based on CRISPR/Cas", "ACS Synthetic Biology", Aug. 26, 2013, pp. 604-613, vol. 2.

Lee, S.-W., et al., "Improved Production of N-Acetylglucosamine in *Saccharomyces cerevisiae* by Reducing Glycolytic Flux", "Biotechnology and Bioengineering", Jun. 3, 2016, pp. 2524-2528, vol. 113, No. 11.

Liu, Y., et al., "Modular pathway engineering of Bacillus subtilis for improved N-acetylglucosamine production", "Metabolic Engineering", Feb. 19, 2014, pp. 42-52, vol. 23.

Mumberg, D., et al., "Yeast vectors for the controlled expression of heterologous proteins in different genetic backgrounds", "Gene", Jan. 9, 1995, pp. 119-122, vol. 156.

Tan, S.Z., et al., "Controlling Central Carbon Metabolism for Improved Pathway Yields in *Saccharomyces cerevisiae*", "ACS Synthetic Biology", Nov. 6, 2015, pp. 116-124, vol. 5.

* cited by examiner

MICROORGANISM HAVING IMPROVED ABILITY TO PRODUCE N-ACETYLGLUCOSAMINE AS A RESULT OF MODULATING GLYCOLYTIC FLUX

CROSS REFERENCE TO RELATED APPLICATIONS

This application claims priority under 35 U.S.C. § 119 of Korean Patent Application 10-2016-0060920 filed May 18, 2016 and Korean Patent Application No. 10-2017-0059916 filed May 15, 2017. The disclosures of such Korean priority patent applications are hereby incorporated herein by reference in their respective entireties, for all purposes.

TECHNICAL FIELD

The present invention relates to a mutant microorganism having an improved ability to produce N-acetylglucosamine as a result of modulating glycolytic flux, and more particularly to a mutant microorganism in which a gene that encodes phosphofructokinase-2 is disrupted or deleted to reduce glycolytic flux to thereby improve the ability of the microorganism to produce N-acetylglucosamine.

BACKGROUND ART

Glucosamine and its derivatives have recently been used in various applications, including dietary supplements, cosmetics, pharmaceuticals and the like, and thus the market demand therefor has increased. To meet this increased demand, metabolic engineering studies on the production of glucosamine and is derivatives have been actively conducted. One recent study has shown that glucosamine and its derivatives can relieve arthritis, suggesting that the application thereof will be expanded to clinical treatment of arthritis.

However, glucosamine and its derivatives, which are currently produced, are mainly extracted from crustacean shell waste, and thus can cause side effects such as allergic reactions in the human body. Accordingly, there have been attempts to produce glucosamine and its derivatives in strains recognized as safe strains. For example, the production of glucosamine by use of *Bacillus subtilis* has been reported (Liu Y, Zhu Y, Li J, Shin H D, Chen R R, Du G, Liu L, Chen J. 2014. Modular pathway engineering of *Bacillus subtilis* for improved N-acetylglucosamine production. Metab Eng 23:42-52).

Methods of effectively producing metabolites such as glucosamine in microorganisms include a method that redirects flux from competing pathways toward a desired target metabolite. One example may be a method of controlling central carbon metabolism to reduce glycolytic flux and increase the yield of the target metabolite. As a method for controlling glycolytic flux, a study has been reported indicating that glycolytic flux is controlled by modulating irreversible enzymes, such as hexokinase, phosphofructokinase and pyruvate kinase, in bacteria.

However, the regulation of glycolysis in eukaryotic cells considerably differs from the regulation of glycolysis in prokaryotic cells. Namely, in eukaryotic cells, additional allosteric effects play an important role in the regulation of glycolysis, and thus glycolysis is regulated by a mechanism which is much more complex than that in prokaryotic cells. As a result, studies on the use of eukaryotic cells have not yet shown worthy results. *S. cerevisiae* can be considerably advantageous for the production of glucosamine and its derivatives, due to its advantage of having excellent resistance to various chemical substances. However, studies on *S. cerevisiae* merely include a recent report indicating that the glycolytic flux was regulated by modulating hexokinase activity in *S. cerevisiae* to enhance the production of gluconate (Tan S Z, Manchester S, Prather K L. 2015. Controlling Central Carbon Metabolism for Improved Pathway Yields in *Saccharomyces cerevisiae*. ACS Synth Biol). However, hexokinase, an enzyme catalyzing the first step of glycolysis in *S. cerevisiae*, has a problem in that regulation of the activity of hexokinase is not suitable for producing metabolites, such as glucosamine and its derivatives, in the downstream steps of glycolysis.

Accordingly, the present inventors have made extensive efforts to develop a method for regulation of glycolytic flux, which is suitable for the production of N-acetylglucosamine which is highly useful as an intermediate metabolite of glycolysis. As a result, the present inventors have found that, when the gene encoding phosphofructokinase-2 (PFK-2) is disrupted or deleted in a microorganism having glycolysis and N-acetylglucosamine biosynthesis pathways, N-acetylglucosamine production can be effectively increased, thereby completing the present invention.

PRIOR ART LITERATURE

Patent Documents

Patent document 1: Korean Patent Laid-Open Publication No. 10-2016-0002509

Non-Patent Documents

Non-patent document 1: Brachmann C B, Davies A, Cost G J, Caputo E, Li J, Hieter P, Boeke J D. 1998. Designer deletion strains derived from *Saccharomyces cerevisiae* S288C: a useful set of strains and plasmids for PCR-mediated gene disruption and other applications. Yeast 14(2):115-32.

Non-patent document 2: Mumberg D, Muller R, Funk M. 1995. Yeast vectors for the controlled expression of heterologous proteins in different genetic backgrounds. Gene 156(1):119-22.

Non-patent document 3: Fahim Farzadfard, Samuel D Perli, Timothy K Lu. 2013. Tunable and Multifunctional Eukaryotic Transcription Factors Based on CRISPR/Cas. ACS Synthetic Biology Vol. 2 No. 10 604-617.

DISCLOSURE OF INVENTION

Technical Problem

An object of the present invention is to provide a mutant organism having an improved ability to produce N-acetylglucosamine, and a method of preparing N-acetylglucosamine using the mutant organism.

Technical Solution

To achieve the above object, the present invention provides a mutant microorganism having an improved ability to produce N-acetylglucosamine in which a gene encoding phosphofructokinase-2 (PFK-2) is disrupted or deleted in a microorganism having glycolysis and N-acetylglucosamine biosynthesis pathways.

The present invention also provides a method for producing N-acetylglucosamine, comprising the steps of: producing N-acetylglucosamine by culturing the above-described mutant microorganism; and recovering the produced N-acetylglucosamine.

Advantageous Effects

The mutant microorganism according to the present invention has advantages in that it has high resistance to various chemical substances, grows rapidly, is easily cultured, and produces N-acetylglucosamine with high efficiency, indicating that it is useful for production of a large amount of N-acetylglucosamine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, an experiment was performed to construct a mutant microorganism having an increased ability to produce N-acetylglucosamine, by reducing glycolytic flux in a microorganism having glycolysis and N-acetylglucosamine (GlcNAc) biosynthesis pathways.

The inhibition of fructose-1,6-biphosphatase (F16BPase) by fructose-2,6-biphosphate (F26BP) and the allosteric activity of PFK-1 are known as major mechanisms that regulate glycolysis and gluconeogenesis in various eukaryotic systems, including S. cerevisiae. These mechanisms differ from those in bacteria in which PFK-1 and F16BPase are regulated transcriptionally by various transcription factors.

To produce N-acetylglucosamine (GlcNAc) from fructose-6-phosphate (6BP), genes such as GFA1, GNA1 and HAD phosphatase are required. In a previous study, the present inventors identified a GFA1 mutant having an excellent ability to produce GlcN6P, and YqaB which is haloacid dehydrogenase-like (HAD) phosphatase, and the present inventors induced the overproduction of N-acetylglucosamine by overexpressing the GFA1 mutant and YqaB in S. cerevisiae.

The GFA1 mutant contains amino acid mutations of Q96H and Q157R in an amino acid sequence of SEQ ID NO: 3, and may preferably have an amino acid sequence of any one of SEQ ID NOs: 4 to 6.

The present inventors have constructed a mutant strain library by introducing each of HAD phosphatase-encoding genes into a strain having the GFA1 mutant introduced therein, and could screen a mutant strain that overproduces N-acetylglucosamine (GlcNAc). In addition, the sequence of HAD phosphatase introduced in the mutant strain that most efficiently overproduces N-acetylglucosamine (GlcNAc) was analyzed, and as a result, it could be seen that the sequence of HAD phosphatase is YqaB having a sequence of SEQ ID NO: 7.

Figure 2:
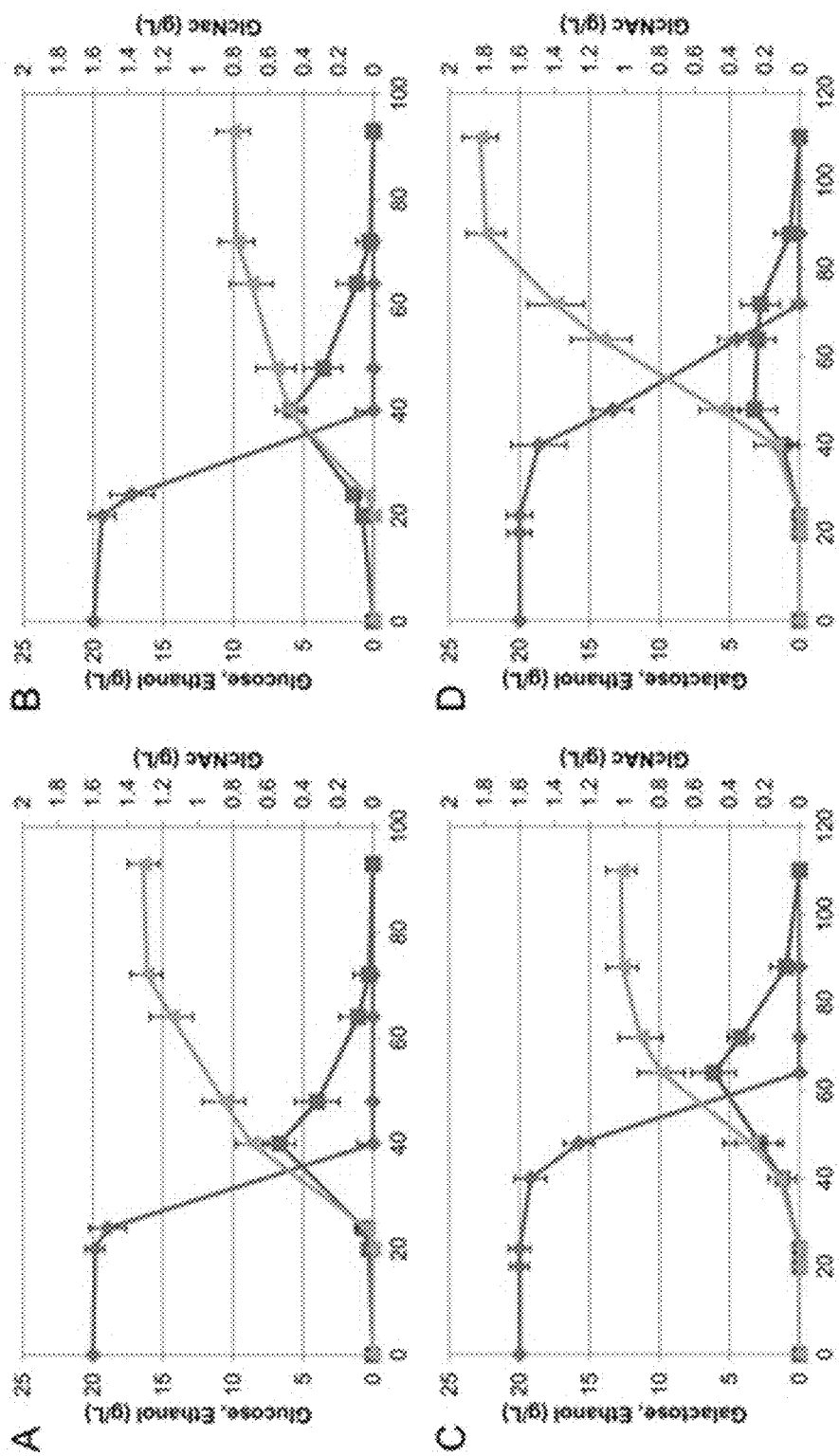
FIG. 2, in graphs A through D, shows the glucose consumption, ethanol production and N-acetylglucosamine production profiles of a BY4742 YM strain (graphs A and C) and a pfk26/pfk27 YM strain (graphs B and D), cultured in minimal media (blue: glucose (graphs A and B)) or galactose ((graphs C and D); red: ethanol; green: N-acetylglucosamine).

In a previous study, the present inventors cloned the GFA1 mutant and HAD phosphatase by use of a single-copy plasmid for screening an efficient enzyme. However, in the present invention, in order to maximize the production of N-acetylglucosamine (GlcNAc), a recombinant vector was constructed using a multicopy plasmid. As a result, it could be seen that, when the GFA1 mutant was overexpressed, the production of N-acetylglucosamine (GlcNAc) was 0.2 g/L, and when the GFA1 mutant was overexpressed together with YqaB, the production of N-acetylglucosamine (GlcNAc) increased up to 1.2 g/L (FIG. 2, graph A). The production of N-acetylglucosamine (GlcNAc) was started with glucose consumption and continued until ethanol would be completely consumed (FIG. 2, graph A).

Figure 1:
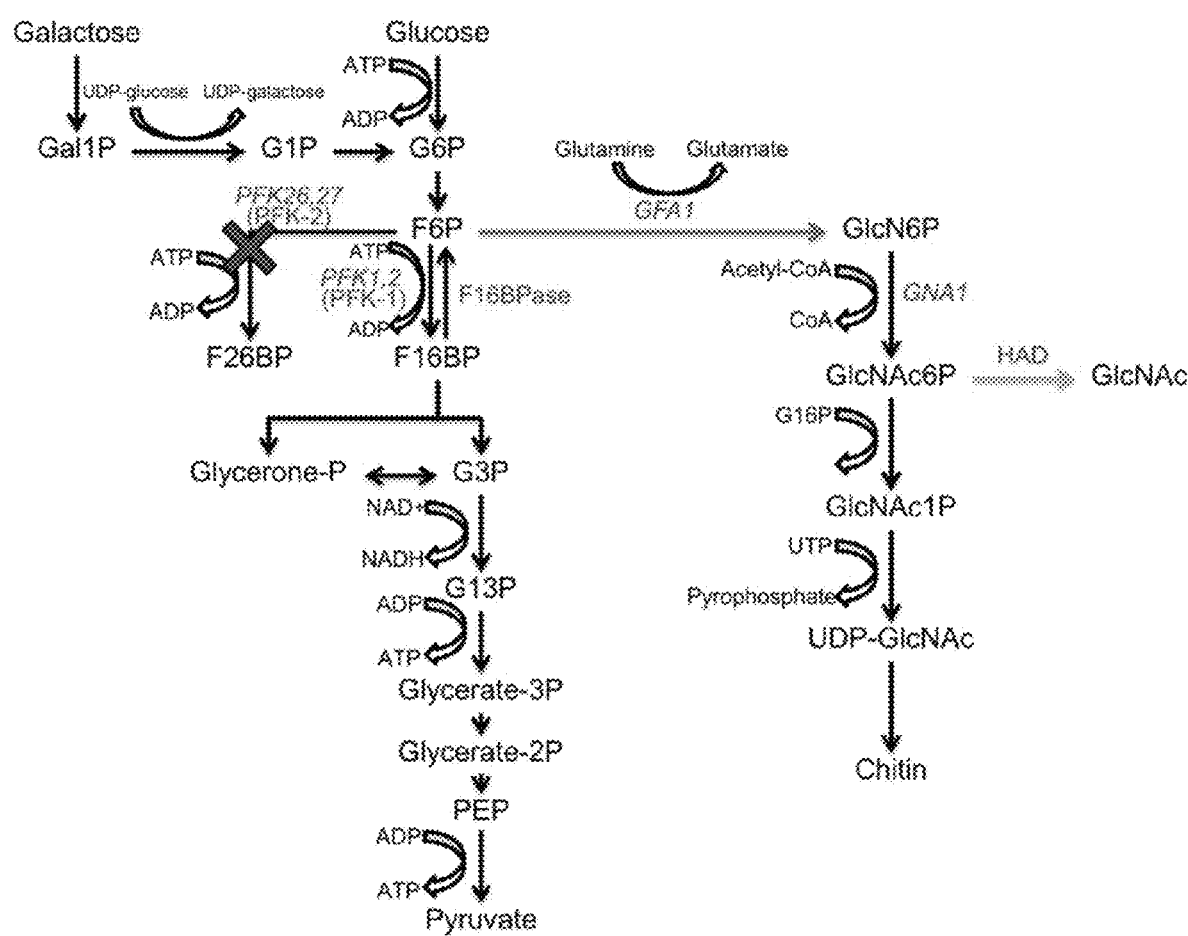
FIG. 1 shows an N-acetylglucosamine biosynthesis pathway.

In an experiment in which PFK26 and PFK27, which encode PFK-2 isozyme, were deleted from S. cerevisiae, it was shown that formation of F26BP was completely eliminated and formation of F16BP was also reduced, suggesting that in vivo PFK-1 activity is decreased when its potent activator F26BP is absent. In the N-acetylglucosamine (GlcNAc) biosynthesis pathway, the first rate-limiting step is regulated by glutamine-fructose-6-phosphate transaminase (Gfa1p) which also uses fructose-6-phosphate (F6P) as a substrate to compete with PFK-1 (FIG. 1). From this characteristic, the present inventors have found that production of N-acetylglucosamine (GlcNAc) can be increased by reducing glycolytic flux in S. cerevisiae.

Eukaryotic PFK-1 is activated by F26BP, and has a much lower $K_M$ value ($K_M$=0.11 mM for F6P with 20 μM F26BP and $K_M$=1.65 mM without F26BP) when F26BP is present. The concentration of F26BP in S. cerevisiae is correlated with glucose 6-phosphate (G6P), and fermentable sugars rapidly increase G6P concentrations to thereby F26BP. Therefore, the present inventors assumed that, because activated PFK-1 has lower $K_M$ value than Gfa1p for F6P ($K_M$(PFK-1)=0.11 mM with 20 μM F26BP vs $K_M$(Gfa1p)= 0.39 mM), the activation of PFK-1 by F26BP upon glucose consumption can interfere with the production of N-acetylglucosamine (GlcNAc). Thus, to reduce PFK-1 activity and increase the production of N-acetylglucosamine (GlcNAc), both the PFK26 and PFK27 genes were deleted so as to eliminate the production of F26BP.

To this end, the present inventors have constructed a pfk26/pfk27 YM strain (Table 1) that overexpresses two acetylglucosamine (GlcNAc) synthesis genes (GFA1 mutant and YqaB) and that shows no PFK-2 activity, and the present inventors have examined the effect of PFK-2 disruption, which leads to PFK-1 deactivation, on the production of N-acetylglucosamine (GlcNAc). As a result, it was shown that rate of glucose consumption (BY4742 YM: 1.28 g/L/h;

pfk26/pfk27 YM: 1.16 g/L/h) and the amount of ethanol produced not greatly differ from those shown by a BY4742 YM control strain and that the production of N-acetylglucosamine (GlcNAc) was slightly lowered (FIG. 2, graphs A and B). Accordingly, the present inventors assumed that glycolytic flux is still strong in the pfk26/pfk27 strain when glucose is a sole carbon source and that an additional decrease in glycolytic flux is required to improve the production of N-acetylglucosamine (GlcNAc).

When S. cerevisiae was cultured using galactose as a sole carbon source, the sugar utilization rate was reduced and ethanol production was reduced, compared to when glucose was used. For this reason, the present inventors used galactose as a sole carbon source in order to reduce the ethanol flux and to increase N-acetylglucosamine production. However, it was shown that, when galactose was used as a sole carbon source, the production of N-acetylglucosamine (GlcNAc) slightly decreased compared to when glucose was used (FIG. 2, graphs A and C). Furthermore, it was shown that the slower glycolytic rate of galactose had no great effect on ethanol production. This is presumably because the anticipated activity of PFK-1 was only slightly reduced while the activity of F16BPase was elevated by reduced F26BP level when galactose was used, which can trigger a futile cycle between F6P and F16BP. The decrease in N-acetylglucosamine (GlcNAc) production when using galactose as a sole carbon source resembled the effect of PFK-2 disruption (FIG. 2, graph B).

Meanwhile, in the pfk26/pfk27 strain grown with glucose as a sole carbon source, the present inventors assumed that the anticipated activity of PFK-1 was reduced but still strong while the activity of F16BPase, which is allosterically inhibited by F26BP, was activated by the disruption of PFK-2, which can also result in a futile cycle.

However, when the effects of galactose as a carbon source and PFK-2 disruption were combined, N-acetylglucosamine (GlcNAc) production was significantly elevated, and also reduced rate of galactose consumption (BY4742 YM: 0.985 g/L/h; pfk26/pfk27 YM: 0.553 g/L/h) and reduced ethanol production were observed (FIG. 2, graph D). The effect of galactose as the sole carbon source in the PFK-2-disrupted strain was noticeable, presumably because enough reduction of glycolysis and activation of gluconeogenesis were achieved. In this situation, F6P can be utilized more by Gfa1p, which has a higher affinity for F6P than deactivated PFK-1, resulting in more flux toward N-acetylglucosamine (GlcNAc) and its higher production. This result suggests that N-acetylglucosamine (GlcNAc) production can be additionally improved by further reducing glycolytic flux with different methods in a PFK-2-disrupted strain.

Figure 3:
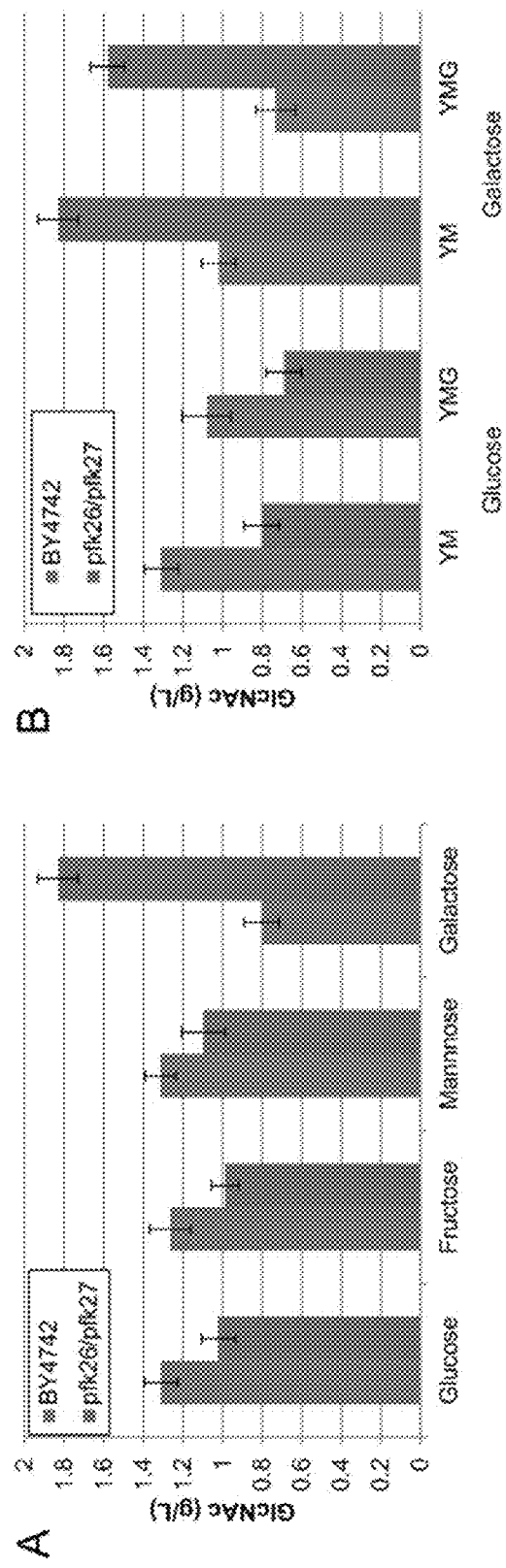
FIG. 3, in graphs A and B, shows the effects of various carbon sources (graph A) and GNA1 overexpression (graph B) on N-acetylglucosamine production.

Meanwhile, the same experiment was performed using various carbon sources other than galactose. As a result, it was shown that glucose, fructose and mannose showed similar final titers of N-acetylglucosamine (GlcNAc) (FIG. 3, graph A). In view of study results indicating that PFK27 was upregulated when carbon sources such as glucose or fructose were used, but was not upregulated when galactose was used, it is thought that suppression of glycolytic gene activation when galactose was used is responsible for improved N-acetylglucosamine (GlcNAc) production.

Based on study results indicating that overexpression of GNA1 originated from S. cerevisiae in bacteria increased N-acetylglucosamine (GlcNAc) production in bacteria, additional overexpression of GNA1, encoding glucosamine-6-phosphate acetyltransferase, was conducted in both a BY4742 YMG strain and a pfk26/pfk27 YMG strain. However, it was shown that the overexpression of GNA1 slightly reduced N-acetylglucosamine (GlcNAc) production compared to that in a strain in which GNA1 was not overexpressed (FIG. 3, graph B). Accordingly, the present inventors could see that GNA1 is expressed sufficiently without up-regulation in S. cerevisiae and that overexpression of the GFA1 mutant and YqaB is essential and sufficient for N-acetylglucosamine (GlcNAc) production.

In the present invention, it has been found that, when glycolytic flux was reduced by disrupting PFK-2 (which produces F26BP that is the most potent activator of PFK-1 in S. cerevisiae) and using galactose as a sole carbon source, ethanol production was reduced and N-acetylglucosamine (GlcNAc) production was increased up to 2 g/L. This is the highest titer of N-acetylglucosamine reported in eukaryotic system.

Therefore, in one aspect, the present invention is directed to a mutant microorganism having an improved ability to produce N-acetylglucosamine in which a gene encoding phosphofructokinase-2 (PFK-2) is disrupted or deleted in a microorganism having glycolysis and N-acetylglucosamine biosynthesis pathways.

In one embodiment of the present invention, the gene encoding phosphofructokinase-2 (PFK-2) may be PFK26 gene represented by SEQ ID NO: 1 and/or PFK27 gene represented by SEQ ID NO: 2.

In one embodiment of the present invention, the mutant microorganism may further have introduced therein a gene encoding a mutant enzyme which comprises a mutation of Q96H and/or Q157R in a GFA1 enzyme represented by SEQ ID NO: 3, and which has an amino acid sequence of any one of SEQ ID NOs: 4 to 6.

In one embodiment of the present invention, the mutant microorganism may have introduced therein a gene encoding HAD phosphatase. The gene encoding HAD phosphatase may be YqaB or YihX. In the meantime, the HAD phosphatase YqaB may be represented by SEQ ID NO: 7.

In one embodiment of the present invention, as a host microorganism, any microorganism can be used without limitations as long as it has glycolysis and N-acetylglucosamine biosynthesis pathways, but any one microorganism selected from the group consisting of yeast, fungus, and *aspergillus* is preferably used.

In another aspect, the present invention is directed to a method for producing N-acetylglucosamine, comprising the steps of: producing N-acetylglucosamine by culturing the above-described mutant microorganism; and recovering the produced N-acetylglucosamine.

In one embodiment of the present invention, the mutant microorganism may be cultured in the presence of galactose as a carbon source.

Meanwhile, according to the present invention, when other kind of glycolysis-regulating genes such as phosphofructokinase or pyruvate kinase is further modified in addition to disrupting or deleting the gene encoding phosphofructokinase-2 (PFK-2), the rate of glycolysis can be reduced, and the production of N-acetylglucosamine (GlcNAc) can further be increased.

Figure 5:
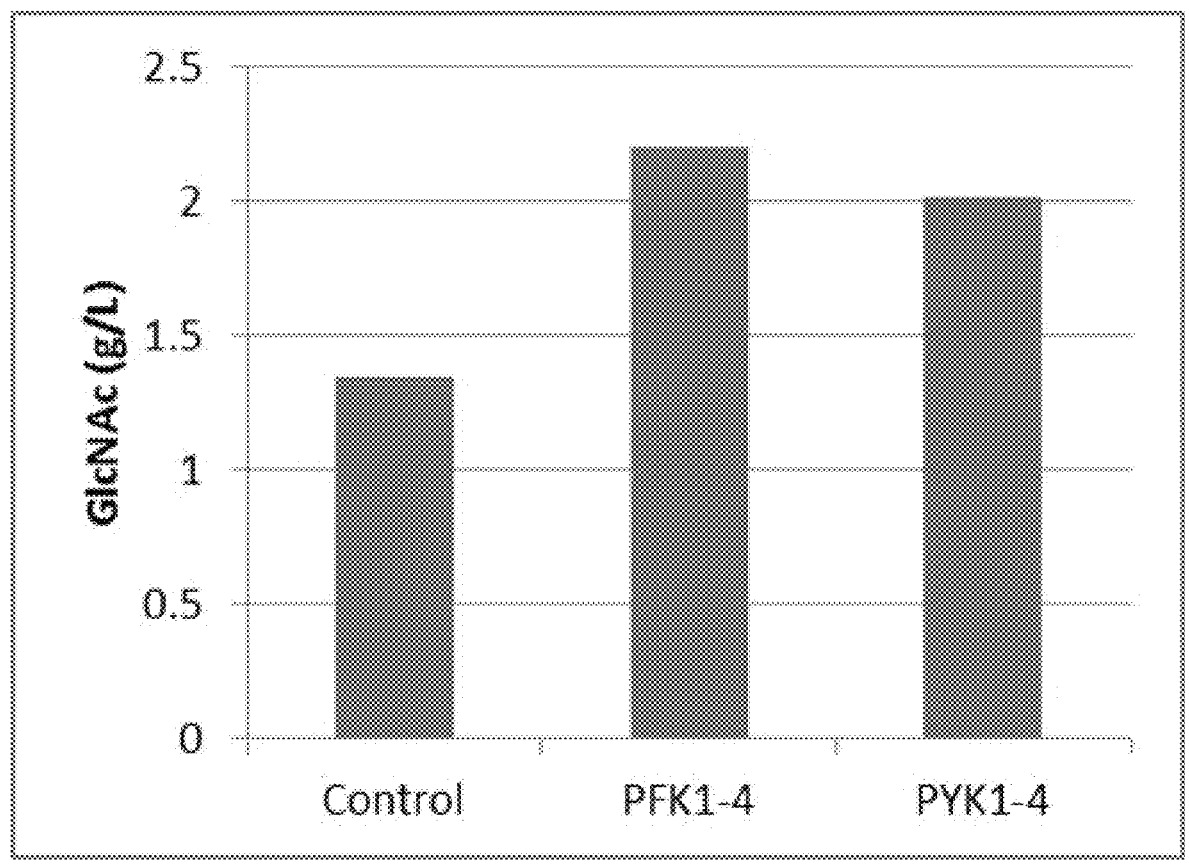
FIG. 5 shows results indicating that N-acetylglucosamine production is increased by reducing expression of PFK-1 and/or Pyk1p by CRIPR/Cas9.

To this end, in the present invention, examination was performed to determine whether N-acetylglucosamine production in the mutant strain containing a deletion of PFK-2 (i.e., pfk26/pfk27) would be increased when expression of PFK1 and/or PYK1 in the mutant strain was additionally inhibited by the CRISPR/Cas system. In an example of the present invention, it could be seen that N-acetylglucosamine (GlcNAc) production in a mutant strain, in which pfk26/pfk27 were deleted and expression of PFK1 and/or PYK1 gene was additionally inhibited (reduced), was significantly increased compared to that in the control strain (pfk26/pfk27 YM) in which expression of these genes was not inhibited (reduced) (FIG. 5).

Thus, in the present invention, expression of genes encoding phosphofructokinase-1 (PFK-1) and/or pyruvate kinase (PYK1P) in the mutant microorganism may additionally be reduced.

In the present invention, the expression of the genes may be reduced by using CRISPR/Cas9. gRNA for reducing expression of the gene encoding phosphofructokinase-1 (PFK-1) may be represented by SEQ ID NO: 10, and gRNA for reducing expression of the gene encoding pyruvate kinase (Pyk1p) may be represented by SEQ ID NO: 11.

Generally, the CRISPR/Cas system consists of a complex of the nuclease Cas protein and guide RNA. In the CRISPR/Cas9 system, a single-stranded guide RNA (sgRNA) consisting of a combination of crRNA and tracrRNA, which is guide RNA, may also form complex with the Cas9 protein.

Because the guide sequence of guide RNA has a sequence complementary to a target sequence, it binds to the target gene. Furthermore, the nuclease Cas9 cleaves a site adjacent to a protospacer adjacent motif (PAM) to produce a double strand break (DSB), and the target gene is deleted by the host cell's DNA repair mechanisms that repair the cleaved site.

In the present invention, Cas protein, for example, Cas9 (CRISPR associated protein 9), binds to the RNA scaffold sequence of guide RNA to form a complex, and recognizes a PAM sequence present in the target gene sequence to guide the CRISPR/Cas system to the target gene, and the target gene is recognized by complementary binding between the guide sequence of guide RNA and the target gene. Finally, the Cas protein exhibits nuclease activity by its active domains (HNH domain and RuvC domain).

It is known that, when one mutation is introduced into a specific amino acid in the two domains, which are involved in nucleotide cleavage, among various domains of Cas9, Cas9 loses its nuclease activity. For example, when the amino acids at positions 10 and 840 in the amino acid sequence of Cas9 of *Streptococcus pyogenes* are mutated into alanine residues (D10A and H840A mutations), the Cas9 loses its DNA cleavage ability, and this catalytically inactive form of Cas9 is usually referred to as dCas9. Furthermore, a Cas9 enzyme, in which only any one of amino acids at positions 10 and 840 is mutated into alanine (D10A or H840A mutation), is known to have nickase activity that cleaves one strand of double-strand DNA.

In the present invention, Cas protein and guide RNA may be constructed such that they will be expressed by a single vector or different vectors when they are simultaneously introduced into a strain. The expressed Cas protein and guide RNA may spontaneously form a complex after their expression in the strain. The term "complex" may be used interchangeably with terms such as "CRISPR/Cas system", "CRISPR complex", "Cas9-gRNA complex", "CRISPR/Cas complex", "Cas protein complex", etc.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Construction of Plasmids and the PFK26/PFK27 Double Knockout Strains Using the method disclosed in Korean Patent Publication No. 10-2016-0002509, a mutant strain that overexpresses a GFA1 mutant and the HAD phosphatase YqaB was constructed, and a pfk26/pfk27 strain containing a deletion of PFK26 and PFK27 for a disruption of PFK-2 was also constructed. Specifically, in order to construct a high-copy plasmid for enhancing the N-acetylglucosamine biosynthesis pathway, a target gene was amplified by PCR, cleaved with restriction enzymes, and then ligated into a p423GPD or p425GPD plasmid. The YqaB gene was cloned into p423GPD having an HIS3 selectable marker, thereby constructing p423GPD-YqaB, and mutated GFA1 and GNA1 were cloned into p425GPD having a LEU2 selectable marker, thereby constructing p425GPD-MG. Overexpressions of YqaB, mutated GFA1 and GNA1 were induced by GPD, GPD and TEF promoters, respectively. The ORF (open reading frame) of PFK26 in *S. cerevisiae* BY4742 was replaced with an integration fragment containing a KanMX6 selectable marker flanked by 45-bp homology arms and loxP sequences via homologous recombination. The KanMX6 selectable marker was recycled using the Cre/loxP system to delete PFK27. Integration and recycling of the selectable marker on the chromosomal locus of either PFK26 or PFK27 were confirmed by sequencing. The constructed strains and plasmids are shown in Tables 1 and 2 below.

TABLE 1

| Strain | Description | Source |
| --- | --- | --- |
| BY4742 | MATα his3Δ1 leu2Δ0 lys2Δ0 ura3Δ0 | (Brachmann et al. 1998) |
| pfk26/pfk27 | BY4742 pfk26Δ0 pfk27::URA3 | — |
| BY4742 YM | BY4742 p423GPD-YqaB p425GPD-GFA1m | — |
| BY4742 YMG | BY4742 p423GPD-YqaB p425GPD-MG | — |
| pfk26/pfk27 YM | pfk26/pfk27 p423GPD-YqaB p425GPD-GFA1m | — |
| pfk26/pfk27 YMG | pfk26/pfk27 p423GPD-YqaB p425GPD-MG | — |

TABLE 2

| Plasmid | Description | Source |
| --- | --- | --- |
| p423GPD | Plasmid with 2μ origin, GPD promoter, CYC1 terminator, and HIS3 selectable marker | (Mumberg et al. 1995) |
| p425GPD | Plasmid with 2μ origin, GPD promoter, CYC1 terminator, and LEU2 selectable marker | (Mumberg et al. 1995) |
| p423GPD-YqaB | p423GPD harboring YqaB | — |
| p425GPD-GFA1m | p423GPD harboring GFA1 mutant | — |
| p425GPD-MG | p423GPD harboring GFA1 mutant under GPD promoter and GNA1 under TEF promoter | — |

Example 2: Culture of Strains for Production of N-Acetylglucosamine

Each of the strains constructed in Example 1 was cultured using a minimal synthetic medium containing 20 g/L of a carbon source (glucose, fructose, mannose or galactose), 6.7 g/L of a yeast nitrogen base (w/o amino acid) and a CSM-HIS-LEU dropout mixture. Each strain was shake-cultured in a 250-ml flask containing 20 mL of the medium at 30° C. and 250 rpm under a microaerobic condition, and the absorbance at a wavelength of 660 nm was measured to check growth.

Example 3: Determination of Metabolite Concentration

Extracellular N-acetylglucosamine production, carbon source consumption and ethanol production were determined by high-performance liquid chromatography (HPLC). The medium, in which each strain was cultured, was centrifuged, and the supernatant was analyzed by HPLC (YL instrument, Anyang, Korea). Glucose, galactose, ethanol and N-acetylglucosamine were detected using an RI detector and 10 mM $H_2SO_4$ solution as an eluent with a Shodex SUGAR SH1011 column (8.0×300 mm).

As a result, the pfk27/pfk27 YM strain produced almost two-fold more N-acetylglucosamine (GlcNAc) compared to the control BY4742 YM strain when cultured using galactose as a sole carbon source (GlcNAc) (FIG. 2, graphs A through D). Meanwhile, glucose, fructose and mannose showed similar final titers of N-acetylglucosamine (GlcNAc) measured 6 days after inoculation of the mutant strain (FIG. 3, graph A), and the mutant strain that further overexpressed GNA1 in addition to the GFA1 mutant and YqaB showed a decrease in the production of N-acetylglucosamine (GlcNAc) in both the glucose and galactose minimal media (FIG. 3, graph B).

From the above-described results, it could be seen that, when the mutant microorganism, obtained by additionally deleting phosphofructokinase-2 from the microorganism having introduced therein the YqaB gene and the GFA1 mutant, was cultured using galactose as a sole carbon source, it showed the highest efficiency in N-acetylglucosamine (GlcNAc) production.

Figure 4:
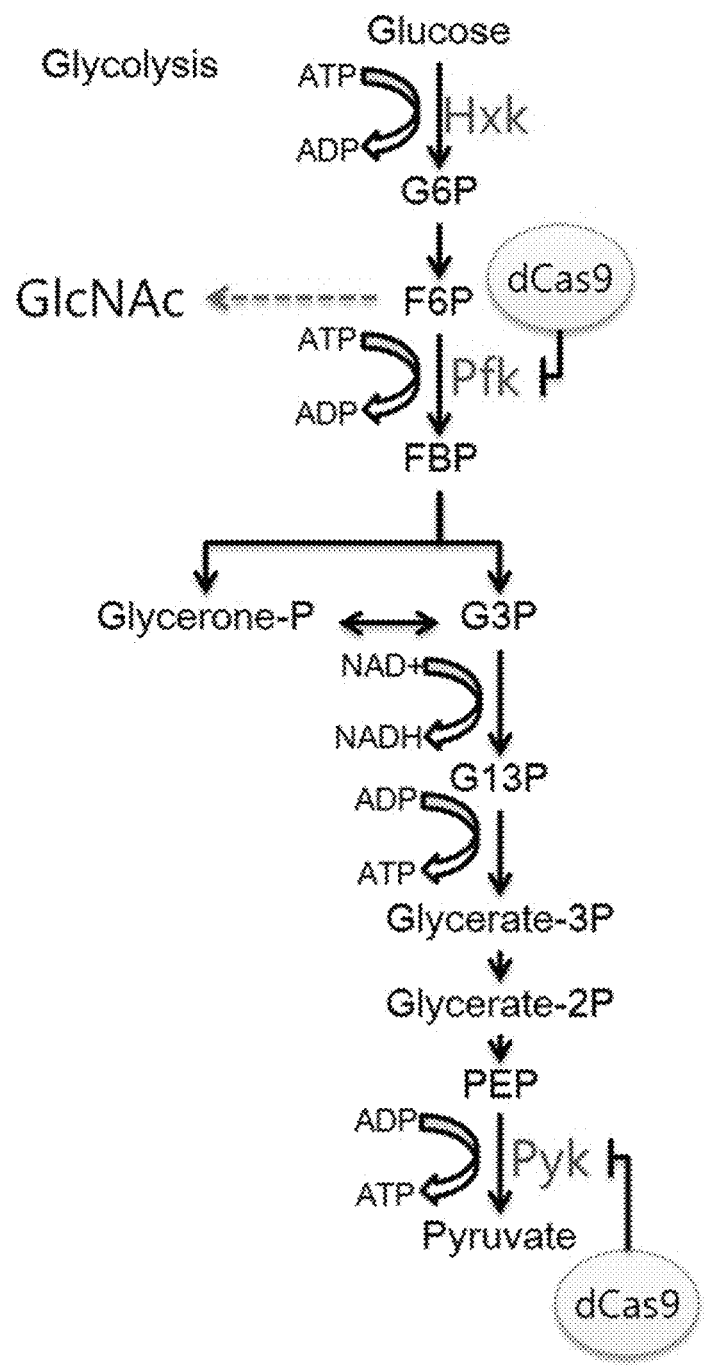
FIG. 4 shows a schematic diagram of glycolysis, in which glycolytic flux is modulated by reducing expression of PFK-1 and/or Pyk1p by CRIPR/Cas9.

Example 4: Construction of a Strain in which Expression of PFK1 and/or PYK1 Gene was Inhibited Using CRISPR/Cas System, and Determination of Metabolite Concentration Examination was performed to determine whether N-acetylglucosamine production in mutant strain constructed in Example 1 in which pfk26/pfk27 were deleted (pfk26/pfk27 YM) would be increased when expression of PFK1 and/or PYK1 gene in the mutant strain was further inhibited or reduced (disrupted) using the CRISPR/Cas system (FIG. 4).

To inhibit or reduce (disrupt) expression of PFK1 and/or PYK1 gene by CRISPR/Cas9, the method disclosed in the article "Tunable and Multifunctional Eukaryotic Transcription Factors Based on CRISPR/Cas (ACS Synthetic Biology Vol. 2 No. 10 604p-617p, Fahim Farzadfard et al.)" was used.

Because the glycolytic gene PFK1 (SEQ ID NO: 8) and/or PYK1 (SEQ ID NO: 9) could not be completely inactivated, guide RNA sequences capable of inhibiting the expression level of the genes to certain levels, thereby increasing N-acetylglucosamine production were screened.

As a result, CAATCTCAAGATTCATGCTA (SEQ ID NO: 10) was selected as a gRNA sequence that binds to the ORF of PFK1, and CAGTAGAAAACACTTTGTGA (SEQ ID NO: 11) was selected as a gRNA sequence that binds to the upstream region of PYK1. The pRPR1_gRNA_handle_RPR1t plasmid (Addgene, USA) and pTPGI_dCas9_VP64 (Addgene, USA) used in the above-described article were purchased, and the gRNA sequences thereof and dCas9 were cloned and expressed according to the manufacturer's instruction, thereby inhibiting expression of the PFK1 and/or PYK1 gene.

As a result, N-acetylglucosamine (GlcNAc) production in the strains (PFK1-4 and PYK1-4), in which expression of these genes was additionally inhibited, was significantly increased compared to that in the control strain (pfk26/pfk27 YM) in which expression of these genes was not inhibited (FIG. 5).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

The invention claimed is:

1. A mutant *Saccharomyces cerevisiae* BY4742 that overproduces N-acetylglucosamine when cultured in the presence of galactose as a sole carbon source, said mutant *Saccharomyces cerevisiae* BY4742 comprising a gene encoding a mutant enzyme comprising the amino acid sequence of SEQ ID NO: 4, SEQ ID NO: 5, or SEQ ID NO: 6, wherein genes pfk26 and pfk27 which encode phosphofructokinase-2 (PFK-2) are disrupted or deleted, wherein the gene pfk26 has the nucleotide sequence of SEQ ID NO: 1 and the gene pfk27 has the nucleotide sequence of SEQ ID NO: 2, and wherein expression of the genes encoding phosphofructokinase-1 (PFK-1) and/or pyruvate kinase (Pyk1p) is inhibited, but not completely inactivated, said mutant *Saccharomyces cerevisiae* BY4742 comprising a Cas protein and/or a vector for expression of Cas protein, and guide RNA for reducing expression of said genes encoding phosphofructokinase-1 (PFK-1) and/or pyruvate kinase (Pyk1p), wherein said guide RNA comprises gRNA of SEQ ID NO: 10 for reducing expression of the gene encoding phosphofructokinase-1 (PFK-1) and/or gRNA of SEQ ID NO: 11 for reducing expression of the gene encoding pyruvate kinase (Pyk1p).

2. The mutant *Saccharomyces cerevisiae* of claim 1, wherein a gene encoding HAD phosphatase YqaB represented by SEQ ID NO: 7 is introduced.

3. A method for producing N-acetylglucosamine, comprising the steps of: producing N-acetylglucosamine by culturing the mutant *Saccharomyces cerevisiae* of claim 1; and recovering the produced N-acetylglucosamine.

4. The method of claim 3, wherein the mutant *Saccharomyces cerevisiae* is cultured in the presence of galactose as a carbon source.

5. The mutant *Saccharomyces cerevisiae* of claim 1, wherein said Cas protein is Cas9.

6. The mutant *Saccharomyces cerevisiae* of claim 1, wherein said Cas protein is in a Cas protein complex.

7. The mutant *Saccharomyces cerevisiae* of claim 1, wherein said genes pfk26 and pfk27 are deleted.

8. The mutant *Saccharomyces cerevisiae* of claim 7, wherein said Cas protein is Cas9.

9. The mutant *Saccharomyces cerevisiae* of claim 7, wherein said Cas protein is in a Cas protein complex.

* * * * *

UNITED STATES PATENT AND TRADEMARK OFFICE
CERTIFICATE OF CORRECTION

PATENT NO.       : 10,724,015 B2
APPLICATION NO.  : 15/598045
DATED            : July 28, 2020
INVENTOR(S)      : Min-Kyu Oh It is certified that error appears in the above-identified patent and that said Letters Patent is hereby corrected as shown below:

On the Title Page

On Page 2, under (56) References Cited, Other Publications, third entry:
"Bloes, E. et al." should be -- Boles, E. et al. --

Signed and Sealed this
Eighth Day of September, 2020

Andrei Iancu
*Director of the United States Patent and Trademark Office*

SEQUENCE LISTING

<160> NUMBER OF SEQ ID NOS: 11

<210> SEQ ID NO 1
<211> LENGTH: 2484
<212> TYPE: DNA
<213> ORGANISM: Saccharomyces cerevisiae

<400> SEQUENCE: 1

```
atgttcaaac cagtagactt ctctgaaaca tctcctgtgc cgcctgatat tgatcttgct        60
cctacacaat ctccacacca tgtggcacct agtcaagact ccagttatga tcttttatcc       120
cggagttccg atgataaaat tgatgctgaa aagggtccgc atgatgaatt atctaagcac       180
ttaccacttt ttcagaaaag accttttgagc gatactccta tatcgagcaa ttggaactct       240
cctggaatca ctgaagaaaa tacaccttct gactctcctg aaaatagcgc tactaatttg       300
aaatcgctac atcgattgca tattaacgac gaaacgcaac taaaaaatgc taaaattccc       360
acaaacgata ctactgacta catgcctcct tcagatggag caaatgaggt aactcggatt       420
gatttgaaag acattaaatc acctacgaga caccataaaa gaagacctac caccatcgat       480
```

```
gttcctggtt taacaaagtc taaaacatct ccagatggtc tcatatcaaa ggaagatagt      540
ggatcaaagt tagtgattgt catggtcgga ctgccagcta cgggaaagtc atttattaca      600
aataaattat ccagattttt aaattattct ttatactatt gtaaagtgtt taatgtcggt      660
aacactagaa ggaagtttgc taaggagcat ggcctaaagg accaggattc aaagttttc      720 gagccgaaaa acgccgactc tactaggttg agagacaaat gggccatgga tactctggat      780
gaattgctag attatttatt agaaggttca ggatctgtgg aattttttga tgctacaaat      840
acctctcgtg aaagaagaaa aaacgttctg gctagaatca gaaagagaag tcctcatttg      900
aaggttttat ttttagaatc tgtttgttcg gatcatgcac tggtacagaa aaatattaga      960
ctcaaattat ttggtccaga ttacaaaggt aaagatcctg aaagctcttt aaaagatttt     1020
aaaagtcgcc tggcaaacta cttgaaagcc tatgaaccaa ttgaggatga cgaaaatttg     1080
cagtacatca aaatgataga tgtgggaaag aaagtcatcg catacaatat tcaagggttt     1140
ttagcttcgc agacggtata ttatttgtta aatttcaatt tggctgacag acaaatttgg     1200
ataacgagaa gtggcgagag cgaagataat gttagtggcc gtataggcgg aaattcccat     1260
ttgactcctc gtggtctaag atttgctaaa agtctaccaa aattcattgc cagacagaga     1320
gaaatatttt atcaaaatct catgcaacaa aaaagaata atgaaaatac agatgggaac     1380
atttataatg acttttcgt ttggaccagc atgcgtgcta ggactatagg gactgctcaa     1440
tatttcaacg aagatgatta tcctatcaaa caaatgaaaa tgttagatga gttaagtgca     1500
ggtgattatg atggtatgac atatccagaa attaaaaaca actttcctga agaattcgaa     1560
aaaagacaga aagataagtt gagatacaga taccctggta ttggcggtga atcgtatatg     1620
gacgttatta atagactcag acctgttatc acagaactag aaagaatcga ggataacgtt     1680
cttattatta cacccgggt ggtggcaaga gccttattgg gttattttat gaacttgagt     1740
atgggtatta ttgccaattt ggatgtccca ttacattgtg tatattgcct agaaccaaaa     1800
ccatatggaa tcacttggtc attatgggag tatgatgaag catcggattc attttctaag     1860
gtcccacaaa cggacttgaa taccaccaga gtaaggagg ttggccttgt ttataatgaa     1920
agaagatatt ctgttatacc aacagctccg ccaagtgcaa gaagcagctt tgcaagtgac     1980
tttttgtcaa gaaaaagatc taatcctact tctgcatctt catcccagag tgaattatca     2040
gaacaaccca gaatagcgt tagtgctcaa actggcagca ataataccac tctcattggg     2100
agcaacttta acatcaagaa tgaaaatggt gattcgagaa taccattatc tgcaccactt     2160
atggccacta atacttctaa taacatctta gatggtggag gtacctcaat ttcgatacat     2220
cgtcccaggg ttgttccaaa tcaaaacaac gtgaatcctc ttttggctaa caacaataaa     2280
gcggcttcta atgtacctaa tgtaaagaag tcagcggcta caccaaggca aatttttgaa     2340
atagataaag tggacgaaaa gttatccatg ttgaaaaata aagttttct attacatgga     2400 aaggattatc ctaataatgc tgataataat gacaacgaag atataagggc aaaaaccatg     2460
aatcgcagcc aaagtcacgt ttaa                                             2484
```

<210> SEQ ID NO 2
<211> LENGTH: 1194
<212> TYPE: DNA
<213> ORGANISM: Saccharomyces cerevisiae

<400> SEQUENCE: 2

```
atgggtggtt cttccgattc agactctcac gatggatatt tgacttccga atataattcc      60
tcgaattctc ttttttcact taacaccggt aacagctatt caagcgcatc tctcgacaga     120
```

```
gccactttag attgtcaaga ttctgttttt ttcgataatc acaaaagttc actgctgtct    180
acagaggtcc caaggtttat ttctaacgac ccgttacact tacccattac actgaattac    240
aaaagagaca atgcagaccc tacgtataca aatggaaaag ttaacaagtt tatgattgtt    300
ttgattgggc taccagctac tgggaagtct accatttctt ctcatttaat tcaatgtttg    360
aagaacaatc cgctaactaa ttcattacgc tgtaaagttt ttaatgctgg taagataaga    420
aggcaaatca gttgtgctac catttcaaag cctttgcttt tgtcgaatac atcttcggaa    480
gacttattta atccgaaaaa taacgataaa aaggaaacgt atgccaggat cactttgcaa    540
aagttgtttc acgaaatcaa caacgatgaa tgtgacgtgg aatcttcga cgccacaaat     600 tcgaccatcg aaagaagaag atttatattt gaggaggttt gttcgttcaa tacagatgag    660
ctttctagtt tcaatttggt gcccataatc ttacaggtgt catgttttaa cagaagcttt    720
atcaaataca atatccacaa taaatcgttt aatgaagact acttagacaa accttatgaa    780
cttgccatca aagattttgc aaagagatta aacattact attcgcagtt tacacctttc     840
tcccttgatg agttcaatca aatccatcga tatatcagcc aacatgaaga aatcgatacg    900
agcttatttt tcttcaatgt tattaatgcg ggcgtcgttg agccacattc tttaaatcaa    960
agtcattacc cttcaacctg cggcaagcaa attagggaca ccattatggt tattgaaaat    1020
ttcatcaatc actattctca gatgtttggt tttgaataca tcgaagctgt taaattgttt    1080
tttgaaagtt ttggaaatag ctcagaggaa actttaacta cactagactc tgttgttaat    1140
gataaatttt tgatgatttt gcagagccta attgaaagca acggatttgc ttga          1194
```

<210> SEQ ID NO 3
<211> LENGTH: 717
<212> TYPE: PRT
<213> ORGANISM: Saccharomyces cerevisiae

<400> SEQUENCE: 3

```
Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu
    50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Thr His Gly Arg Pro Glu Gln
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
    130                 135                 140

Ala Lys Leu Tyr Leu His Leu Tyr Asn Thr Asn Leu Gln Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
```

```
                    180                 185                 190
Ile Ala Thr Arg Lys Gly Ser Pro Leu Leu Ile Gly Val Lys Ser Glu
                195                 200                 205
Lys Lys Leu Lys Val Asp Phe Val Asp Val Glu Phe Pro Glu Glu Asn
        210                 215                 220
Ala Gly Gln Pro Glu Ile Pro Leu Lys Ser Asn Asn Lys Ser Phe Gly
225                 230                 235                 240
Leu Gly Pro Lys Lys Ala Arg Glu Phe Glu Ala Gly Ser Gln Asn Ala
                245                 250                 255
Asn Leu Leu Pro Ile Ala Ala Asn Glu Phe Asn Leu Arg His Ser Gln
        260                 265                 270
Ser Arg Ala Phe Leu Ser Glu Asp Gly Ser Pro Thr Pro Val Glu Phe
            275                 280                 285
Phe Val Ser Ser Asp Ala Ala Ser Val Val Lys His Thr Lys Lys Val
        290                 295                 300
Leu Phe Leu Glu Asp Asp Leu Ala His Ile Tyr Asp Gly Glu Leu
305                 310                 315                 320
His Ile His Arg Ser Arg Arg Glu Val Gly Ala Ser Met Thr Arg Ser
                325                 330                 335
Ile Gln Thr Leu Glu Met Glu Leu Ala Gln Ile Met Lys Gly Pro Tyr
                340                 345                 350
Asp His Phe Met Gln Lys Glu Ile Tyr Glu Gln Pro Glu Ser Thr Phe
            355                 360                 365
Asn Thr Met Arg Gly Arg Ile Asp Tyr Glu Asn Asn Lys Val Ile Leu
        370                 375                 380
Gly Gly Leu Lys Ala Trp Leu Pro Val Val Arg Arg Ala Arg Arg Leu
385                 390                 395                 400
Ile Met Ile Ala Cys Gly Thr Ser Tyr His Ser Cys Leu Ala Thr Arg
                405                 410                 415
Ala Ile Phe Glu Glu Leu Ser Asp Ile Pro Val Ser Val Glu Leu Ala
            420                 425                 430
Ser Asp Phe Leu Asp Arg Lys Cys Pro Val Phe Arg Asp Asp Val Cys
            435                 440                 445
Val Phe Val Ser Gln Ser Gly Glu Thr Ala Asp Thr Met Leu Ala Leu
        450                 455                 460
Asn Tyr Cys Leu Glu Arg Gly Ala Leu Thr Val Gly Ile Val Asn Ser
465                 470                 475                 480
Val Gly Ser Ser Ile Ser Arg Val Thr His Cys Gly Val His Ile Asn
                485                 490                 495
Ala Gly Pro Glu Ile Gly Val Ala Ser Thr Lys Ala Tyr Thr Ser Gln
                500                 505                 510
Tyr Ile Ala Leu Val Met Phe Ala Leu Ser Leu Ser Asp Asp Arg Val
            515                 520                 525
Ser Lys Ile Asp Arg Arg Ile Glu Ile Ile Gln Gly Leu Lys Leu Ile
        530                 535                 540
Pro Gly Gln Ile Lys Gln Val Leu Lys Leu Glu Pro Arg Ile Lys Lys
545                 550                 555                 560
Leu Cys Ala Thr Glu Leu Lys Asp Gln Lys Ser Leu Leu Leu Leu Gly
                565                 570                 575
Arg Gly Tyr Gln Phe Ala Ala Ala Leu Glu Gly Ala Leu Lys Ile Lys
            580                 585                 590
Glu Ile Ser Tyr Met His Ser Glu Gly Val Leu Ala Gly Glu Leu Lys
            595                 600                 605
```

```
His Gly Val Leu Ala Leu Val Asp Glu Asn Leu Pro Ile Ile Ala Phe
            610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Ile Cys Asn Glu Asn Asp
                645                 650                 655

Glu Val Trp Ala Gln Lys Ser Lys Ser Ile Asp Leu Gln Thr Leu Glu
            660                 665                 670

Val Pro Gln Thr Val Asp Cys Leu Gln Gly Leu Ile Asn Ile Ile Pro
        675                 680                 685

Leu Gln Leu Met Ser Tyr Trp Leu Ala Val Asn Lys Gly Ile Asp Val
    690                 695                 700

Asp Phe Pro Arg Asn Leu Ala Lys Ser Val Thr Val Glu
705                 710                 715
```

<210> SEQ ID NO 4
<211> LENGTH: 717
<212> TYPE: PRT
<213> ORGANISM: Artificial Sequence
<220> FEATURE:
<223> OTHER INFORMATION: GFA1 mutant 1

<400> SEQUENCE: 4

```
Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Lys Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Lys Glu
50                  55                  60

Glu Ile Thr Lys Gln Asn Pro Asn Arg Asp Val Thr Phe Val Ser His
65                  70                  75                  80

Cys Ser Ile Ala His Thr Arg Trp Ala Thr His Gly Arg Pro Glu His
                85                  90                  95

Val Asn Cys His Pro Gln Arg Ser Asp Pro Glu Gly Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Leu Glu Leu Glu
                165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
        195                 200                 205

Lys Lys Leu Lys Val Asp Phe Val Asp Val Glu Phe Pro Glu Glu Asn
210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255
```

```
Asn Leu Leu Pro Ile Ala Ala Asn Glu Phe Asn Leu Arg His Ser Gln
            260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
    290                 295                 300

Leu Phe Leu Glu Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile His Thr Leu Glu Met Glu Leu Ala Gln Ile Met Lys Gly Pro Tyr
            340                 345                 350

Asp His Phe Met Gln Lys Glu Ile Tyr Glu Gln Pro Glu Ser Thr Phe
        355                 360                 365

Asn Thr Met Arg Gly Arg Ile Asp Tyr Glu Asn Asn Lys Val Ile Leu
    370                 375                 380

Gly Ser Leu Lys Ala Trp Leu Pro Val Val Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
            420                 425                 430

Ser Asp Phe Leu Asp Arg Lys Cys Pro Val Phe Arg Asp Asp Val Cys
        435                 440                 445

Val Phe Val Ser Gln Ser Gly Glu Thr Ala Asp Thr Met Leu Ala Leu
    450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495

Ala Gly Pro Glu Ile Gly Val Ala Ser Thr Lys Ala Tyr Thr Ser Gln
            500                 505                 510

Tyr Ile Ala Leu Val Met Phe Ala Leu Ser Leu Ser Asp Asp Arg Val
        515                 520                 525

Ser Ile Ile Asp Arg Arg Ile Glu Ile Gln Gly Leu Lys Leu Ile
530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
                565                 570                 575

Arg Gly Tyr Gln Phe Ala Ala Leu Glu Gly Ala Leu Lys Ile Lys
            580                 585                 590

Glu Ile Ser Tyr Val His Ser Glu Gly Val Leu Ala Gly Glu Leu Lys
        595                 600                 605

His Gly Val Leu Ala Leu Val Asp Glu Asn Leu Pro Ile Ile Ala Phe
    610                 615                 620

Gly Thr Arg Asp Ser Leu Phe Pro Lys Val Val Ser Ile Glu Gln
625                 630                 635                 640

Val Thr Ala Arg Lys Gly His Pro Ile Ile Cys Asn Glu Asn Asp
                645                 650                 655

Glu Val Trp Ala Arg Lys Ser Lys Ser Ile Asp Leu Gln Thr Leu Glu
            660                 665                 670
```

```
Val Pro Gln Thr Val Asp Cys Leu Gln Gly Leu Ile Asn Ile Ile Pro
            675                 680                 685

Leu Gln Leu Met Ser Tyr Trp Leu Ala Val Asn Lys Gly Ile Asp Val
        690                 695                 700

Asp Phe Pro Arg Asn Leu Ala Lys Ser Val Thr Val Glu
705                 710                 715

<210> SEQ ID NO 5
<211> LENGTH: 717
<212> TYPE: PRT
<213> ORGANISM: Artificial Sequence
<220> FEATURE:
<223> OTHER INFORMATION: GFA1 mutant 2

<400> SEQUENCE: 5

Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Asp Glu Ala Asp
        35                  40                  45

Ser Thr Phe Ile Tyr Lys Gln Ile Gly Lys Val Ser Ala Leu Glu Glu
    50                  55                  60

Glu Ile Thr Lys Gln Asn Pro Asn Arg Asp Ala Thr Phe Val Ser His
65                  70                  75                  80

Cys Gly Ile Ala His Thr Arg Trp Ala Thr His Gly Arg Pro Glu His
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
    130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Glu Leu Glu
                165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
        195                 200                 205

Lys Lys Leu Lys Val Asp Phe Val Asp Val Glu Phe Pro Glu Glu Asn
    210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Asn Ala Ala Asn Glu Phe Asn Leu Arg His Ser Gln
            260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
    290                 295                 300

Leu Phe Leu Glu Asp Asp Asp Leu Ala His Ile Tyr Asp Gly Glu Leu
305                 310                 315                 320
```

His Ile His Arg Ser Arg Arg Glu Val Gly Ala Ser Met Thr Arg Ser
            325                 330                 335

Ile Gln Thr Leu Glu Met Glu Ser Ala Gln Ile Met Lys Gly Pro Tyr
        340                 345                 350

Asp His Phe Met Gln Lys Glu Ile Tyr Glu Gln Pro Glu Ser Thr Phe
    355                 360                 365

Asn Thr Met Arg Gly Arg Ile Asp Tyr Glu Asn Asn Lys Val Ile Leu
370                 375                 380

Gly Gly Leu Lys Ala Trp Leu Pro Val Val Arg Ala Arg Arg Leu
385                 390                 395                 400

Ile Met Ile Ala Cys Gly Thr Ser Tyr His Ser Cys Leu Ala Thr Arg
                405                 410                 415

Ala Ile Phe Glu Glu Leu Ser Asp Ile Pro Val Ser Val Glu Leu Ala
            420                 425                 430

Ser Asp Phe Leu Asp Arg Lys Cys Pro Val Phe Arg Asp Asp Val Cys
        435                 440                 445

Val Phe Val Ser Gln Ser Gly Glu Thr Ala Asp Thr Met Leu Ala Leu
    450                 455                 460

Asn Tyr Cys Leu Glu Arg Gly Ala Leu Thr Val Gly Ile Val Asn Ser
465                 470                 475                 480

Val Gly Ser Ser Ile Ser Arg Val Thr His Cys Gly Val His Ile Asn
                485                 490                 495

Ala Gly Pro Glu Ile Gly Val Ala Ser Thr Lys Ala Tyr Thr Ser Gln
            500                 505                 510

Tyr Ile Ala Leu Val Met Phe Ala Leu Ser Leu Ser Asp Asp Arg Val
        515                 520                 525

Ser Lys Ile Asp Arg Arg Ile Glu Ile Ile Gln Gly Leu Lys Leu Ile
530                 535                 540

Pro Gly Gln Ile Lys Gln Val Leu Lys Leu Glu Pro Arg Ile Lys Lys
545                 550                 555                 560

Leu Cys Ala Thr Glu Leu Lys Asp Gln Lys Ser Leu Leu Leu Leu Gly
                565                 570                 575

Arg Gly Tyr Gln Phe Ala Ala Ala Leu Glu Gly Ala Leu Lys Ile Lys
            580                 585                 590

Glu Ile Ser Tyr Met His Ser Glu Gly Val Leu Ala Gly Glu Leu Lys
        595                 600                 605

His Gly Val Leu Ala Leu Val Asp Glu Asn Leu Pro Ile Ile Ala Phe
610                 615                 620

Gly Thr Arg Asp Ser Leu Phe Pro Lys Val Val Ser Ser Ile Glu Gln
625                 630                 635                 640

Val Thr Ala Arg Lys Gly His Pro Ile Ile Cys Asn Glu Asn Asp
                645                 650                 655

Glu Val Trp Ala Gln Lys Ser Lys Ser Ile Asp Leu Gln Thr Leu Glu
            660                 665                 670

Val Pro Gln Thr Val Asp Cys Leu Gln Gly Leu Ile Asn Ile Ile Pro
        675                 680                 685

Leu Gln Leu Met Ser Tyr Trp Leu Ala Val Asn Lys Gly Ile Asp Val
690                 695                 700

Asp Phe Pro Arg Asn Leu Ala Lys Ser Val Thr Val Glu
705                 710                 715

<210> SEQ ID NO 6
<211> LENGTH: 717
<212> TYPE: PRT

<213> ORGANISM: Artificial Sequence
<220> FEATURE:
<223> OTHER INFORMATION: GFA1 mutant 3

<400> SEQUENCE: 6

```
Met Cys Gly Ile Phe Gly Tyr Cys Asn Tyr Leu Val Glu Arg Ser Arg
1               5                   10                  15

Gly Glu Ile Ile Asp Thr Leu Val Asp Gly Leu Gln Arg Leu Glu Tyr
            20                  25                  30

Arg Gly Tyr Asp Ser Thr Gly Ile Ala Ile Asp Gly Glu Ala Asp
        35                  40                  45

Ser Thr Phe Ile Tyr Lys Gln Ile Gly Lys Val Ser Ala Leu Lys Glu
50                  55                  60

Glu Ile Thr Lys Gln Asn Pro Asn Arg Asp Val Thr Phe Val Ser His
65                  70                  75                  80

Cys Gly Ile Ala His Thr Arg Trp Ala Thr His Gly Arg Pro Glu His
                85                  90                  95

Val Asn Cys His Pro Gln Arg Ser Asp Pro Glu Asp Gln Phe Val Val
            100                 105                 110

Val His Asn Gly Ile Ile Thr Asn Phe Arg Glu Leu Lys Thr Leu Leu
        115                 120                 125

Ile Asn Lys Gly Tyr Lys Phe Glu Ser Asp Thr Asp Thr Glu Cys Ile
130                 135                 140

Ala Lys Leu Tyr Leu His Leu Tyr Asn Thr Asn Leu Arg Asn Gly His
145                 150                 155                 160

Asp Leu Asp Phe His Glu Leu Thr Lys Leu Val Leu Leu Glu Leu Glu
                165                 170                 175

Gly Ser Tyr Gly Leu Leu Cys Lys Ser Cys His Tyr Pro Asn Glu Val
            180                 185                 190

Ile Ala Thr Arg Lys Gly Ser Pro Leu Leu Ile Gly Val Lys Ser Glu
        195                 200                 205

Lys Lys Leu Lys Val Asp Phe Val Asp Val Glu Phe Pro Glu Glu Asn
210                 215                 220

Ala Gly Gln Pro Glu Ile Pro Leu Lys Ser Asn Asn Lys Ser Phe Gly
225                 230                 235                 240

Leu Gly Pro Lys Lys Ala Arg Glu Phe Glu Ala Gly Ser Gln Asn Ala
                245                 250                 255

Asn Leu Leu Pro Ile Ala Ala Asn Glu Phe Asn Leu Arg His Ser Gln
            260                 265                 270

Ser Arg Ala Phe Leu Ser Glu Asp Gly Ser Pro Thr Pro Val Glu Phe
        275                 280                 285

Phe Val Ser Ser Asp Ala Ala Ser Val Val Lys His Thr Lys Lys Val
290                 295                 300

Leu Phe Leu Glu Asp Asp Leu Ala His Ile Tyr Asp Gly Glu Leu
305                 310                 315                 320

His Ile His Arg Ser Arg Arg Glu Val Gly Ala Ser Met Thr Arg Ser
                325                 330                 335

Ile Gln Thr Leu Glu Met Val Leu Ala Gln Ile Met Lys Gly Pro Tyr
            340                 345                 350

Asp His Phe Met Gln Lys Glu Ile Tyr Glu Gln Pro Glu Ser Thr Phe
        355                 360                 365

Asn Thr Met Arg Gly Arg Ile Asp Tyr Glu Asn Asn Lys Val Ile Leu
370                 375                 380

Gly Gly Leu Lys Ala Trp Leu Pro Val Val Arg Arg Ala Arg Arg Leu
```

-continued

```
                385                 390                 395                 400
        Ile Met Ile Ala Cys Gly Thr Ser Tyr His Ser Cys Leu Ala Thr Arg
                        405                 410                 415

Ala Ile Phe Glu Glu Leu Ser Asp Ile Pro Val Ser Val Glu Leu Ala
                        420                 425                 430

Ser Asp Phe Leu Asp Arg Lys Cys Pro Val Phe Arg Asp Asp Val Cys
                        435                 440                 445

Val Phe Val Ser Gln Ser Gly Glu Thr Ala Asp Thr Met Leu Ala Leu
                        450                 455                 460

Asn Tyr Cys Leu Glu Arg Gly Ala Leu Thr Val Gly Ile Val Asn Ser
        465                 470                 475                 480

Val Gly Ser Ser Ile Ser Arg Val Thr His Cys Gly Val His Ile Asn
                        485                 490                 495

Ala Gly Pro Glu Ile Gly Val Ala Ser Thr Lys Ala Tyr Thr Ser Gln
                        500                 505                 510

Tyr Ile Ala Leu Val Met Phe Ala Leu Ser Leu Ser Asp Asp Arg Val
                        515                 520                 525

Ser Lys Ile Asp Arg Arg Ile Glu Ile Ile Gln Gly Leu Lys Leu Ile
                        530                 535                 540

Pro Gly Gln Ile Lys Gln Val Leu Lys Leu Glu Pro Arg Ile Lys Lys
        545                 550                 555                 560

Leu Cys Ala Thr Glu Leu Lys Asp Gln Lys Ser Leu Leu Leu Leu Gly
                        565                 570                 575

Arg Gly Tyr Gln Phe Ala Ala Ala Leu Glu Gly Ala Leu Lys Ile Lys
                        580                 585                 590

Glu Ile Ser Tyr Met His Ser Glu Gly Val Leu Ala Gly Glu Leu Lys
                        595                 600                 605

His Gly Val Leu Ala Leu Val Asp Glu Asn Leu Pro Ile Ile Ala Phe
                        610                 615                 620

Gly Thr Arg Asp Ser Leu Phe Pro Lys Val Val Ser Ser Ile Glu Gln
        625                 630                 635                 640

Val Thr Ala Arg Lys Gly His Pro Ile Ile Cys Asn Glu Asn Asp
                        645                 650                 655

Glu Val Trp Ala Gln Lys Ser Lys Ser Ile Asp Leu Gln Thr Leu Glu
                        660                 665                 670

Val Pro Gln Thr Val Asp Cys Leu Gln Gly Leu Ile Asn Ile Pro
                        675                 680                 685

Leu Gln Leu Met Ser Tyr Trp Leu Ala Val Asn Lys Gly Ile Asp Val
                        690                 695                 700

Asp Phe Pro Arg Asn Leu Ala Lys Ser Val Thr Val Glu
        705                 710                 715
```

<210> SEQ ID NO 7
<211> LENGTH: 188
<212> TYPE: PRT
<213> ORGANISM: Escherichia coli

<400> SEQUENCE: 7

```
        Met Tyr Glu Arg Tyr Ala Gly Leu Ile Phe Asp Met Asp Gly Thr Ile
        1               5                   10                  15

Leu Asp Thr Glu Pro Thr His Arg Lys Ala Trp Arg Glu Val Leu Gly
                        20                  25                  30

His Tyr Gly Leu Gln Tyr Asp Ile Gln Ala Met Ile Ala Leu Asn Gly
                        35                  40                  45
```

```
Ser Pro Thr Trp Arg Ile Ala Gln Ala Ile Ile Glu Leu Asn Gln Ala
 50                  55                  60

Asp Leu Asp Pro His Ala Leu Ala Arg Glu Lys Thr Glu Ala Val Arg
 65                  70                  75                  80

Ser Met Leu Leu Asp Ser Val Glu Pro Leu Pro Leu Val Asp Val Val
                 85                  90                  95

Lys Ser Trp His Gly Arg Arg Pro Met Ala Val Gly Thr Gly Ser Glu
                100                 105                 110

Ser Ala Ile Ala Glu Ala Leu Leu Ala His Leu Gly Leu Arg His Tyr
            115                 120                 125

Phe Asp Ala Val Val Ala Asp His Val Lys His His Lys Pro Ala
130                 135                 140

Pro Asp Thr Phe Leu Leu Cys Ala Gln Arg Met Gly Val Gln Pro Thr
145                 150                 155                 160

Gln Cys Val Val Phe Glu Asp Ala Asp Phe Gly Ile Gln Ala Ala Arg
                165                 170                 175

Ala Ala Gly Met Asp Ala Val Asp Val Arg Leu Leu
            180                 185
```

<210> SEQ ID NO 8
<211> LENGTH: 2964
<212> TYPE: DNA
<213> ORGANISM: Saccharomyces cerevisiae

<400> SEQUENCE: 8

```
atgcaatctc aagattcatg ctacggtgtt gcattcagat ctatcatcac aaatgatgaa      60
gctttattca agaagaccat tcactttat cacactctag gatttgcaac tgtgaaagat     120
ttcaacaaat tcaaacatgg tgaaaatagc ttactatctt cagggacttc ccaagattcc     180
ttgagagaag tttggttaga atctttcaag ttgagtgagg ttgatgcttc tgggttccgt     240
ataccacaac aagaagctac taacaaggct caaagtcaag gtgctctatt aaagattcgt     300
ttagtgatgt ctgctccaat cgatgaaact ttcgacacca acgaaaccgc cacaatcact     360
tatttctcta ctgatttgaa caagattgtc gagaaattcc caaaacaagc cgaaaaattg     420
tccgatacct tagtgttttt gaaagatcca atgggcaaca catcaccttc tcaggctta     480 gctaatgcaa ccgattccgc tccaacttcc aaagatgctt tcttagaagc tacctccgaa     540
gacgaaatca tctctagagc ttcttccgat gcttctgact actaagaca acattgggc      600 tcttctcaaa agaagaagaa gattgctgtc atgacttctg gtggtgattc tccaggtatg     660
aatgccgctg ttcgtgccgt tgttcgtaca ggtatacatt tcggctgtga tgtttttgct     720
gtttacgaag gttacgaagg tttactaaga ggcggtaaat atttaaagaa aatggcttgg     780
gaagatgtca gaggttggtt aagtgaaggt ggtactttga ttggtactgc tcgttctatg     840
gaattcagaa agcgtgaggg tcgtagacaa gctgcaggca atttaatttc gcaaggtatt     900
gacgctttgg ttgtttgtgg tggtgatggt tctttaaccg tgctgatct tttcagacac     960 gaatggccat ctttggttga tgaattggtt gcagaaggta gattcactaa agaagaagtc    1020
gccccataca agaatttgtc cattgttggt cttgtcggtt ccatcgataa tgatatgtct    1080
ggtactgact ctaccattgg tgcttattct gctttggaaa gaatctgtga atggttgac    1140 tacattgatg ccaccgctaa atcccactcc cgtgcctttg ttgttgaagt tatgggtaga    1200
cattgtggtt ggttggcctt gatggctggt attgctaccg tgccgatta cattttatt     1260 ccagaaagag ctgttcctca cggaaaatgg caggacgaat tgaaggaagt gtgccaaaga    1320
```

```
cacagaagta agggtagaag aaataacaca attattgtcg ctgaaggtgc tttagatgat    1380
caattaaacc ctgttactgc caatgacgtc aaagatgctt tgattgaatt gggtctagac    1440
accaaggtaa ccattctagg tcacgttcaa agaggtggta cagctgttgc tcatgacaga    1500
tggttagcta ctctacaagg tgtcgatgct gttaaggccg ttctggaatt taccccctgaa   1560 actccttctc cattaattgg tattttagaa aacaagataa ttagaatgcc attggttgaa    1620
tctgtgaagt tgactaaatc tgttgccact gccattgaaa acaaagattt cgataaggca    1680
atttctttaa gagacacaga atttattgaa ctttacgaaa acttcttatc cactaccgtt    1740
aaagatgatg gttccgaatt attgccagta tctgacagac taaacattgg tattgtccat    1800
gttggtgccc catctgctgc tttgaacgct gccacccgtg ccgcaactct atactgtttg    1860
tctcacggcc ataaaccata cgctatcatg aatggtttca gtggattgat tcaaaccggt    1920
gaagtgaagg aactatcatg gattgatgtc gaaaactggc ataacttggg tggttccgaa    1980
atcggtacga acagatctgt tgcttcagaa gatttgggta ccattgctta ctacttccaa    2040
aagaacaagc tagacggttt gattattctt ggtggttttg aaggtttcag gtccttgaag    2100
caattgcgtg acggtagaac ccaacaccca atctttaaca ttccaatgtg tttgattcca    2160
gccactgttt ctaacaacgt tccaggtact gaatactcac ttggtgttga tacctgtttg    2220
aacgcattag tcaattacac tgatgacatc aaacagagtg cttctgcgac aagaagaaga    2280
gtcttcgtct gtgaagtcca agtggtcac tctggttaca tcgcttcttt cactggttta    2340
atcactggtg ctgtttcagt gtacactcca gaaaagaaga tcgacttagc ttctatcaga    2400
gaagatataa ctctattaaa agagaacttt cgtcacgaca aggtgaaaaa cagaaacggt    2460
aagctattgg ttagaaacga acaagcttct agcgtatata gcactcaatt gttggctgac    2520
atcatctctg aagcaagcaa gggtaagttt ggtgttagaa ctgctatccc aggccatgtt    2580
caacaaggtg gtgttccatc ttctaaagac cgtgtcaccg cttccagatt gctgtcaaa    2640 tgtatcaagt ttatcgaaca atggaacaag aaaaatgaag cttctccaaa cactgacgct    2700
aaggttttga gattcaagtt cgatactcac ggtgaaaagg taccaactgt tgagcacgaa    2760
gatgactctg ctgctgttat ctgtgttaat ggttctcacg tttccttcaa gccaattgct    2820
aacctttggg aaaacgaaac caacgttgaa ttaagaaagg gttttgaagt tcactgggct    2880
gaatacaaca agattggtga catcctgtcc ggtagattaa agttgagagc tgaggtagcc    2940
gctttagccg ctgaaaacaa atga                                            2964

<210> SEQ ID NO 9
<211> LENGTH: 1503
<212> TYPE: DNA
<213> ORGANISM: Saccharomyces cerevisiae

<400> SEQUENCE: 9
atgtctagat tagaaagatt gacctcatta aacgttgttg ctggttctga cttgagaaga     60
acctccatca ttggtaccat cggtccaaag accaacaacc cagaaacctt ggttgctttg     120
agaaaggctg gtttgaacat tgtccgtatg aacttctctc acggttctta cgaataccac     180
aagtctgtca ttgacaacgc cagaaagtcc gaagaattgt acccaggtag accattggcc     240
attgctttgg acaccaaggg tccagaaatc agaactggta ccaccaccaa cgatgttgac     300
tacccaatcc caccaaacca cgaaatgatc ttcaccaccg atgacaagta cgctaaggct     360
tgtgacgaca gatcatgta cgttgactac aagaacatca ccaaggtcat ctccgctggt     420
agaatcatct acgttgatga tggtgttttg tctttccaag ttttggaagt cgttgacgac     480
```

```
aagactttga aggtcaaggc tttgaacgcc ggtaagatct gttcccacaa gggtgtcaac        540
ttaccaggta ccgatgtcga tttgccagct ttgtctgaaa aggacaagga agatttgaga        600
ttcggtgtca agaacggtgt ccacatggtc ttcgcttctt tcatcagaac cgccaacgat        660
gttttgacca tcagagaagt cttgggtgaa caaggtaagg acgtcaagat cattgtcaag        720
attgaaaacc aacaaggtgt taacaacttc gacgaaatct tgaaggtcac tgacggtgtt        780
atggttgcca gaggtgactt gggtattgaa atcccagccc agaagtctt ggctgtccaa         840 aagaaattga ttgctaagtc taacttggct ggtaagccag ttatctgtgc tacccaaatg        900
ttggaatcca tgacttacaa cccaagacca accagagctg aagtttccga tgtcggtaac        960
gctatcttgg atggtgctga ctgtgttatg ttgtctggtg aaaccgccaa gggtaactac       1020
ccaatcaacg ccgttaccac tatggctgaa accgctgtca ttgctgaaca agctatcgct       1080
tacttgccaa actacgatga catgagaaac tgtactccaa agccaacctc caccaccgaa       1140
accgtcgctg cctccgctgt cgctgctgtt ttcgaacaaa aggccaaggc tatcattgtc       1200
ttgtccactt ccggtaccac cccaagattg gtttccaagt acagaccaaa ctgtccaatc       1260
atcttggtta ccagatgccc aagagctgct agattctctc acttgtacag aggtgtcttc       1320
ccattcgttt tcgaaaagga acctgtctct gactggactg atgatgttga agcccgtatc       1380
aacttcggta ttgaaaaggc taaggaattc ggtatcttga agaagggtga cacttacgtt       1440
tccatccaag gtttcaaggc cggtgctggt cactccaaca ctttgcaagt ctctaccgtt       1500
taa                                                                    1503

<210> SEQ ID NO 10
<211> LENGTH: 20
<212> TYPE: RNA
<213> ORGANISM: Artificial Sequence
<220> FEATURE:
<223> OTHER INFORMATION: gRNA for binding ORF sequence of PFK1

<400> SEQUENCE: 10
caaucucaag auucaugcua                                                    20

<210> SEQ ID NO 11
<211> LENGTH: 20
<212> TYPE: RNA
<213> ORGANISM: Artificial Sequence
<220> FEATURE:
<223> OTHER INFORMATION: gRNA for binding upstream of PYK1

<400> SEQUENCE: 11
caguagaaaa cacuuuguga                                                    20
```